(12) United States Patent
Singh et al.

(10) Patent No.: US 9,593,119 B2
(45) Date of Patent: *Mar. 14, 2017

(54) PROCESS FOR THE PREPARATION OF DIPEPTIDYLPEPTIDASE INHIBITORS

(71) Applicant: Glenmark Pharmacueticals Limited, Mumbai (IN)

(72) Inventors: Sunil Kumar Singh, Hyderabad (IN); Sachin Srivastava, N. Mumbai (IN); Shekhar Bhaskar Bhirud, Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/076,846

(22) Filed: Mar. 22, 2016

(65) Prior Publication Data

US 2016/0272642 A1   Sep. 22, 2016

Related U.S. Application Data

(62) Division of application No. 14/421,896, filed as application No. PCT/IN2013/000483 on Aug. 6, 2013, now Pat. No. 9,353,114.

(60) Provisional application No. 61/710,548, filed on Oct. 5, 2012.

(30) Foreign Application Priority Data

Dec. 7, 2012   (IN) .......................... 3461/MUM/2012
Aug. 6, 2013   (WO) ................. PCT/IN2013/000483
Aug. 17, 2013   (IN) .......................... 2410/MUM/2012

(51) Int. Cl.
| C07D 473/04 | (2006.01) |
| --- | --- |
| C07D 473/18 | (2006.01) |
| C07D 401/04 | (2006.01) |
| C07D 473/06 | (2006.01) |
| C07C 69/78 | (2006.01) |

(52) U.S. Cl.
CPC ............ C07D 473/18 (2013.01); C07C 69/78 (2013.01); C07D 401/04 (2013.01); C07D 473/04 (2013.01); C07D 473/06 (2013.01)

(58) Field of Classification Search
None
See application file for complete search history.

(56) References Cited

U.S. PATENT DOCUMENTS 7,407,955 B2   8/2008   Himmelsbach et al.
2012/0165525 A1   6/2012   Allegrini et al.

FOREIGN PATENT DOCUMENTS

| CN | 103172633 A | 6/2013 |
| --- | --- | --- |
| CN | 101048409 B | 1/2014 |
| EP | 2468749 A1 | 6/2012 |

OTHER PUBLICATIONS

Blech, Sefan, et al., "The Metabolism and Disposition of the Oral Dipeptidyl Peptidase-4 Inhibitor, Linagliptin, in Humans", Drug Metabolism and Disposition, 2010, vol. 38, No. 4, pp. 667-678.

*Primary Examiner* — Golam M M Shameem
*Assistant Examiner* — Laura Daniel
(74) *Attorney, Agent, or Firm* — Ryan, Mason & Lewis, LLP

(57) ABSTRACT

The present invention provides a process for the preparation of linagliptin, a compound of Formula I, the process comprising deprotecting a compound of Formula II wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

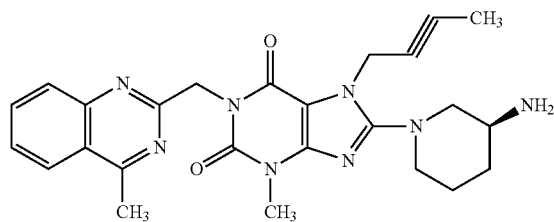

Formula I

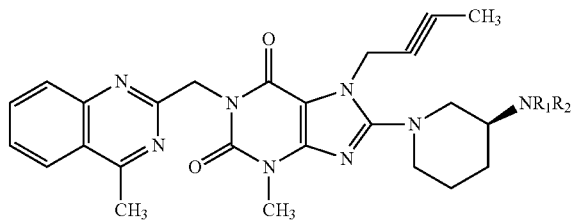

Formula II

5 Claims, 3 Drawing Sheets

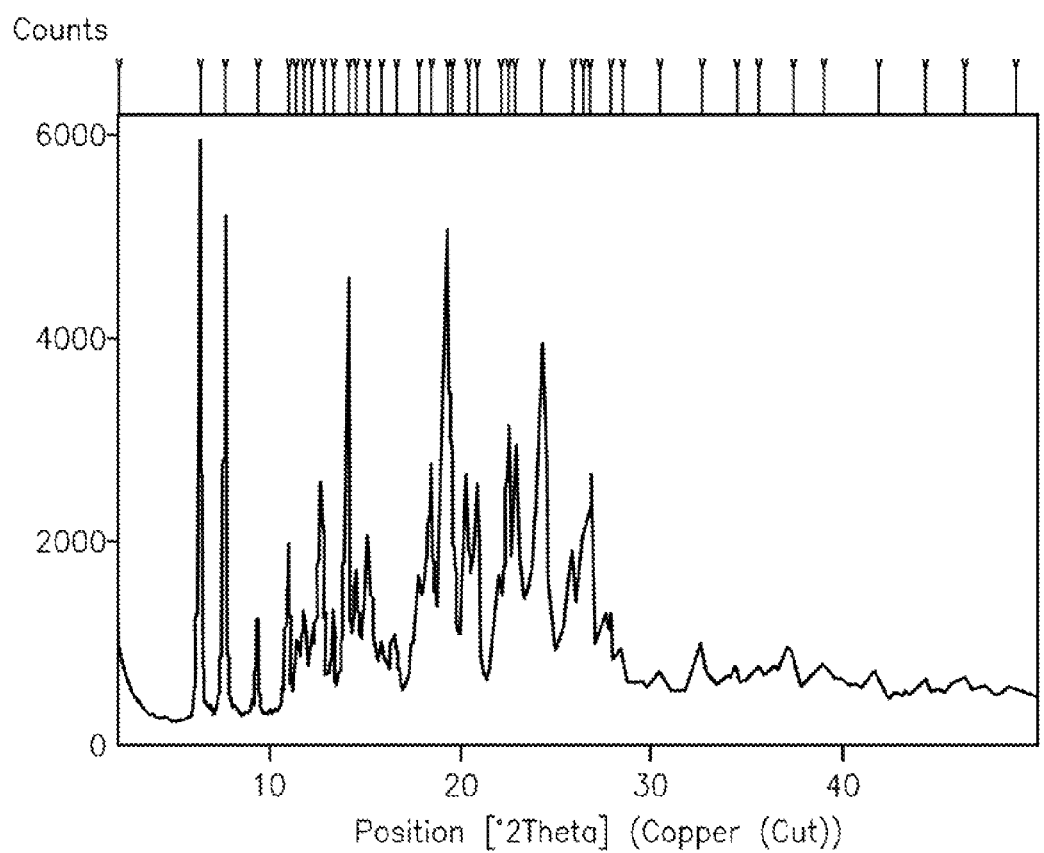
FIG. 1: is an X-ray powder diffraction pattern of compound of Linagliptin dibenzoyl-D-tartaric acid salt.

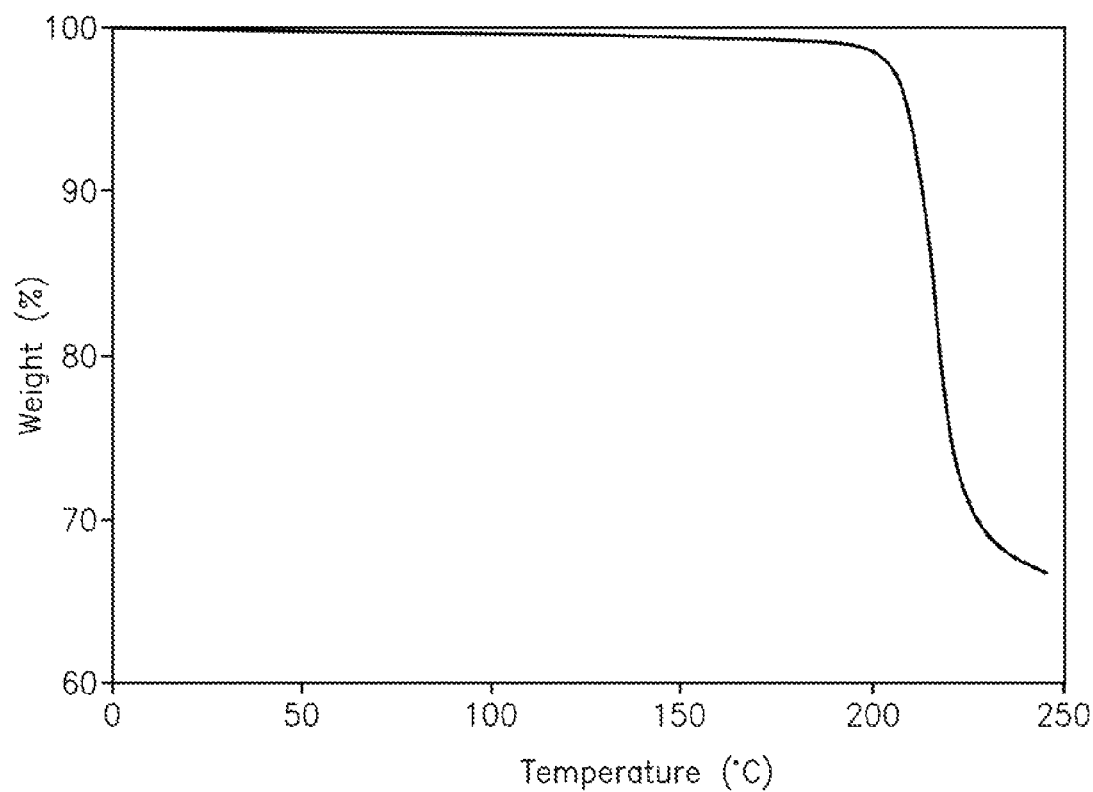
FIG. 2: is Differential scanning calorimetry endotherm of Linagliptin dibenzoyl-D-tartaric acid salt.

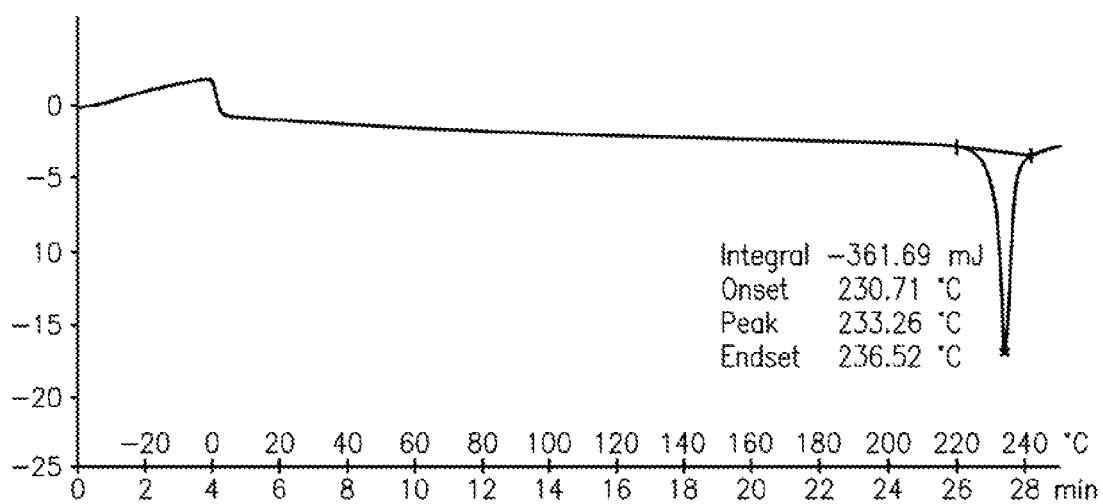
FIG. 3: is Thermogravimetric analysis curve of Linagliptin dibenzoyl-D-tartaric acid salt.

PROCESS FOR THE PREPARATION OF DIPEPTIDYLPEPTIDASE INHIBITORS

PRIORITY

This application is as divisional application of co-pending U.S. Ser. No. 14/421,896 which claims priority under 35 U.S.C. §371 to International Application No. PCT/IN2013/000483, filed Aug. 6, 2013 which claims the benefit under 35 U.S.C. §119 to Indian Provisional Application No. 2410/MUM/2012, filed on Aug. 17, 2012, 3461/MUM/2012 filed on Dec. 7, 2012, and U.S. Provisional Application No. 61/710,548, filed on Oct. 5, 2012, the contents of which are incorporated by reference herein.

FIELD OF THE INVENTION

The present invention relates to a novel process for preparation of dipeptidylpeptidase inhibitors. More specifically the present invention relates to novel compounds of 3-aminopiperidine derivatives and their use as possible intermediates in the preparation of dipeptidylpeptidase inhibitors, like linagliptin and alogliptin.

BACKGROUND OF THE INVENTION

Inhibitors of dipeptidylpeptidase IV, also DPP-IV inhibitors or gliptins, are a class of oral hypoglycemics that block DPP-IV. They can be used to treat diabetes mellitus type 2.

Linagliptin, which is chemically known as 8-[3(R)-Aminopiperidin-1-yl]-7-(2-butynyl)-3-methyl-1-(4-methylquinazolin-2-ylmethyl)xanthine, is represented by compound of Formula I.

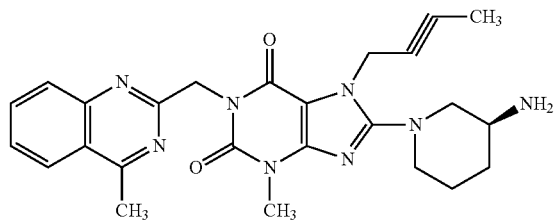 [SMILES: CC#CCn1c(N2CCC[C@H](N)C2)nc2c1c(=O)n(Cc1nc(C)c3ccccc3n1)c(=O)n2C]

TRADJENTA® is Boheringer's (R)-linagliptin 5 mg once daily tablet indicated for type 2 diabetes mellitus as an adjunct to diet and exercise.

Alogliptin chemically known as 2-[6-[3(R)-Aminopiperidin-1-yl]-3-methyl-2,4-dioxo-1,2,3,4-tetrahydropyrimidin-1-ylmethyl]benzonitrile is represented by the structural formula, shown below

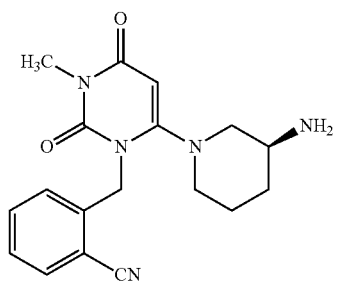 [SMILES: Cn1c(=O)cc(N2CCC[C@H](N)C2)n(Cc2ccccc2C#N)c1=O]

Alogliptin is a dipeptidylpeptidase IV (DPP4) inhibitor approved in Japan for monotherapy and in combination with an alpha-glucosidase inhibitor for the once-daily, oral treatment of type 2 diabetes.

U.S. Pat. No. 7,407,955 (US Pat. '955) discloses linagliptin and process for preparing it. US Pat. '955 discloses process for preparing linagliptin by deprotecting N-BOC protected linagliptin.

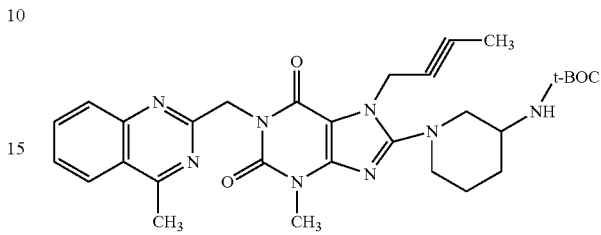

Presently, we have developed a novel process for the preparation of linagliptin which involves deprotecting a compound of Formula II.

Formula II

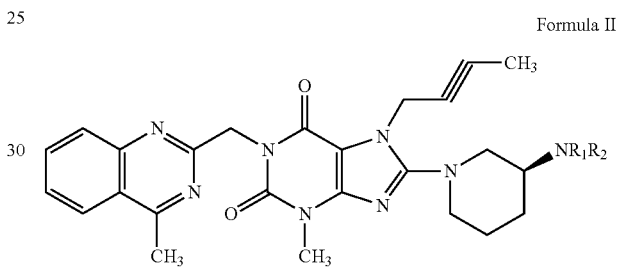

wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

The process of the present invention is novel, commercially advantageous and industrially feasible and leads to the formation of linagliptin in higher yields and purity as compared to the known process.

SUMMARY OF THE INVENTION

The present invention provides a process for the preparation of linagliptin, a compound of Formula I, Formula I

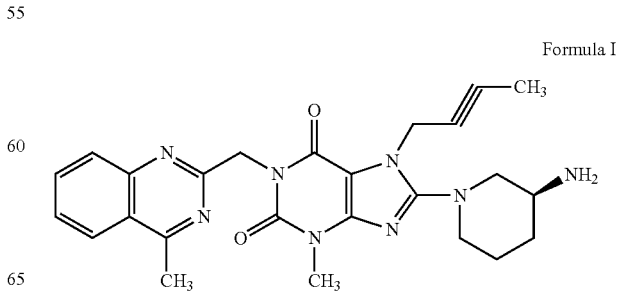

the process comprising deprotecting a compound of Formula II

Formula II

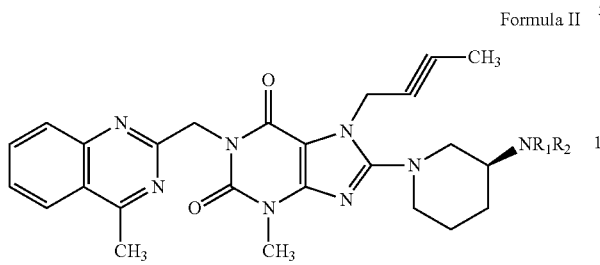

wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

The present invention provides a compound of Formula II

Formula II wherein $R_1$ and $R_2$ are as defined above.

The present invention provides a compound of Formula IV

Formula IV wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

The present invention provides a process for the preparation of a compound of Formula IVA Formula IVA wherein the aromatic ring of the phthalimido group is substituted with one or more $R_3$ substituents selected from the group consisting of halogen, alkyl, nitro and amino; the process comprising reacting R-(3)-aminopiperidine with substituted phthalic anhydride wherein the aromatic ring of the phthalic anhydride is substituted with one or more $R_3$ substituents selected from the group consisting of halogen, alkyl, nitro and amino.

The present invention provides Linagliptin dibenzoyl-D-tartaric acid salt.

The present invention provides use of Linagliptin dibenzoyl-D-tartaric acid for the preparation of linagliptin.

BRIEF DESCRIPTION OF THE FIGURES

FIG. 1: is an X-ray powder diffraction pattern of compound of Linagliptin dibenzoyl-D-tartaric acid salt.

FIG. 2: is Differential scanning calorimetry endotherm of Linagliptin dibenzoyl-D-tartaric acid salt.

FIG. 3: is Thermogravimetric analysis curve of Linagliptin dibenzoyl-D-tartaric acid salt.

DETAILED DESCRIPTION OF THE INVENTION

The present invention provides a process for preparation of linagliptin, a compound of Formula I, Formula I comprising deprotecting a compound of Formula II Formula II wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

The term "halogen" as used herein means iodine, bromine, chlorine and fluorine. The term "alkyl" as used herein includes a straight or branched chain hydrocarbon containing from 1 to 6 carbon atoms. Representative examples of alkyl include, but are not limited to methyl, ethyl, n-propyl, isopropyl, n-butyl, sec-butyl, tert-butyl, n-pentyl, isopentyl, neopentyl, n-hexyl. The term "trialkylsilyl" as used herein includes trimethylsilyl, triethylsilyl and the like. The term "trihaloacetyl" as used herein includes trichloroacetyl, tribromoacetyl, trifluoroacetyl and the like. The term "alkylsulfonyl" as used herein includes methanesulfonyl, ethanesulfonyl and the like. The term "arylsulfonyl" as used herein includes benzenesulfonyl and tosyl and the like.

The aromatic ring of the phthalimido group is substituted with one, two, or more $R_3$ substituents. The $R_3$ substituents may be present in any position of the aromatic ring. Preferably the $R_3$ substituent is an alkyl group present at position 4 of the aromatic ring.

In one embodiment, the present invention provides a process for the preparation of linagliptin, compound of Formula I, the process comprising deprotecting a compound of Formula II wherein the linagliptin is obtained in a yield of at least 85%.

In one embodiment, the present invention provides a process for the preparation of linagliptin, compound of Formula I, the process comprising deprotecting a compound of Formula II wherein the linagliptin is obtained in a yield of at least 85% and/or a chemical purity of at least 95% as determined by HPLC.

In one embodiment, the present invention provides a process for the preparation of linagliptin, compound of Formula I, the process comprising deprotecting a compound of Formula IIA, wherein the aromatic ring of the phthalimido group is substituted with one or more $R_3$ substituents selected from the group consisting of halogen, alkyl, nitro, amino.

Formula IIA

The deprotection of compound of Formula II A may be carried out by using reagents selected from the group consisting of hydrazine, hydrazine hydrate and amines.

The amines for deprotection may be selected from primary amine, secondary amine and tertiary amine which may be unsubstituted or substituted by small functional groups like hydroxy, nitro, halo. Preferably primary amines like methylamine, ethyl amine, ethanolamine are used for deprotection.

The deprotection reaction may be carried out in a solvent selected from the group consisting of alcohols, nitriles, hydrocarbons, halogenated hydrocarbons, ether and water or mixtures thereof.

The alcohol may be selected from the group consisting of methanol, ethanol, propanol, isopropanol, butanol, 2-butanol, isobutanol, pentanol and the like or mixtures thereof.

The nitriles may be selected from the group consisting of acetonitrile, propionitrile and the like.

The hydrocarbon may be selected from the group consisting of hexane, heptane, toluene, benzene and the like. The halogenated hydrocarbon may be selected from the group consisting of methylene dichloride, ethylene dichloride and the like. The ethers may be selected from the group consisting of dioxane, diethyl ether, tetrahydrofuran, tetrahydropyran and the like.

In one embodiment, the present invention provides a process for the preparation of linagliptin, compound of Formula I, the process comprising deprotecting a compound of Formula IIA, wherein $R_3$ is alkyl.

In one embodiment, the present invention provides a process for the preparation of linagliptin, compound of Formula I, the process comprising deprotecting a compound of Formula IIA1.

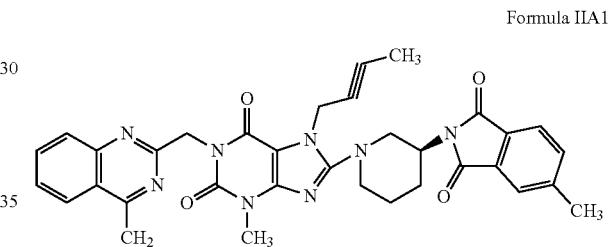

Formula IIA1

In one embodiment, the present invention provides a process for the preparation of linagliptin, compound of Formula I, the process comprising deprotecting a compound of Formula IIA1 with ethanolamine without using additional solvent.

In one embodiment, the present invention provides a process for the preparation of linagliptin, compound of Formula I, the process comprising deprotecting a compound of Formula IIA1 with ethanolamine in a hydrocarbon solvent.

In one embodiment, the present invention provides a process for the preparation of linagliptin, compound of Formula I, the process comprising deprotecting a compound of Formula IIA1 with hydrazine hydrate in an alcoholic solvent.

In one embodiment, the present invention provides a process for deprotecting a compound of Formula II, wherein $R_1$ is H and $R_2$ is trialkylsilyl or trialkylsilylethoxycarbamates, the process comprising using quaternary ammonium compounds such as tetrabutylammonium fluoride in the presence of solvents such as dimethylformamide, tetrahydrofuran and the like in mildly basic conditions.

In one embodiment, the present invention provides a process for deprotecting a compound of Formula II, wherein $R_1$ is H and $R_2$ is acetyl, trihaloacetyl, alkylsulfonyl, arylsulfonyl, diphenylphosphine, the process comprising using an acid or a base.

The acids used for deprotection may be selected from mineral acids like hydrochloric acid, sulfuric acid, nitric acid or organic acids such as acetic acid, methanesulfonic acid, trichloroacetic acid, p-toluene sulfonic acid and the like.

The base used for deprotection may be selected from inorganic base or organic base. The inorganic base may be selected from the group consisting of alkali metal hydroxides such as sodium hydroxide, potassium hydroxide, barium hydroxide and lithium hydroxide and the like; metal carbonates such as sodium carbonate, potassium carbonate, magnesium carbonate, and calcium carbonate and the like; metal bicarbonates such as sodium bicarbonate, and potassium bicarbonate; metal hydrides such as lithium hydride, sodium hydride, and potassium hydride and the like; borohydrides such as sodium borohydride, potassium borohydride; and bases such as lithium aluminium hydride and ammonia. The organic base may be selected from the group consisting of organic amines such as triethylamine, diisopropylethylamine, N,N-dimethylaniline, pyridine, 4-dimethylaminopyridine, tri-n-butylamine, N-methylmorpholine, piperidine and the like; alkali metal alkoxides such as sodium methoxide, sodium ethoxide, sodium-tert-butoxide, potassium methoxide, potassium ethoxide, potassium-tert-butoxide lithium methoxide, lithium ethoxide, lithium-tert-butoxide and the like.

In one embodiment, the present invention provides a process for deprotecting a compound of Formula II wherein $R_1$ is H and $R_2$ is 9-fluorenylmethoxycarbonyl, the process comprising using organic amines such as piperidine, morpholine, piperazine and the like.

In one embodiment, the present invention provides a process for deprotecting a compound of Formula II wherein $R_1$ is H and $R_2$ is trityl, the process comprising using mild acids such as trifluoroacetic acid, trichloroacetic acid or by using 1-hydroxy-1-H benzotriazole. The reaction may be carried out in solvent selected from halogenated hydrocarbon or trifluoroethanol.

In one embodiment, the present invention provides a process for deprotecting a compound of Formula II wherein $R_1$ is H and $R_2$ is sulfonylethoxycarbonyl, the process comprising using inorganic bases as described above.

In one embodiment, the present invention provides a compound of Formula II

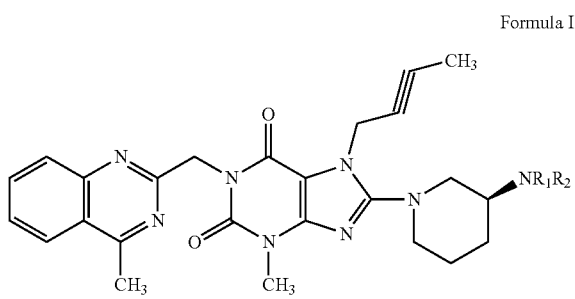

Formula II wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

In one embodiment, the present invention provides a compound of Formula IIA, wherein the aromatic ring of the phthalimido group is substituted with one or more $R_3$ substituents selected from the group consisting of halogen, alkyl, nitro, amino.

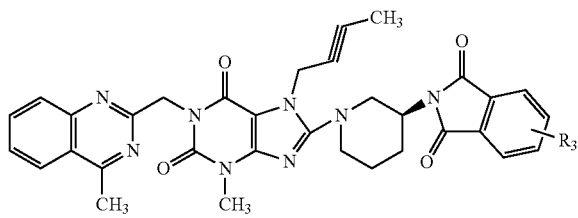

Formula IIA

In one embodiment, the present invention provides a compound of Formula IIA, wherein $R_3$ is alkyl.

The alkyl group may be selected from the group consisting of methyl, ethyl, n-propyl, isopropyl, n-butyl, sec-butyl, tert-butyl, n-pentyl, isopentyl, neopentyl, n-hexyl and the like and may be present at one or more positions of the aromatic ring. Preferably the alkyl group is methyl and it is present in the $4^{th}$ position of the aromatic ring.

In one preferred embodiment, the present invention provides a compound of Formula IIA1.

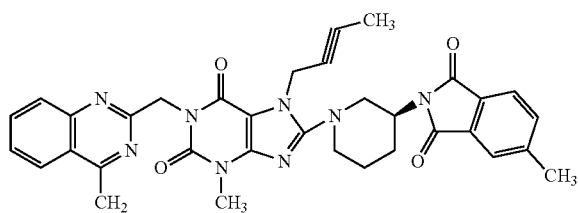

Formula IIA1

In one embodiment, the present invention provides a compound of Formula II, wherein $R_1$ is H and $R_2$ is acetyl, represented below.

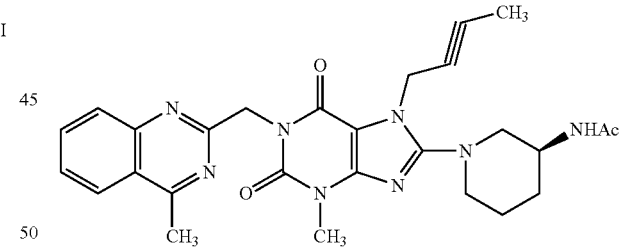

In one embodiment, the present invention provides a compound of Formula II, wherein $R_1$ is H and $R_2$ is trihaloacetyl, preferably trifluoroacetyl, represented below.

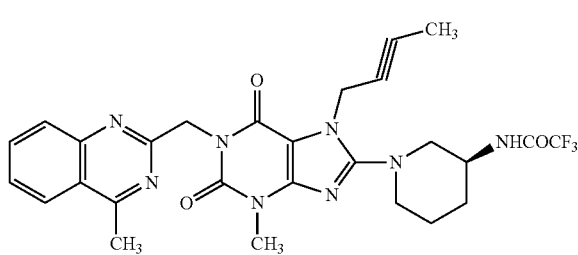

In one embodiment, the present invention provides a process, for the preparation of a compound of Formula II Formula II

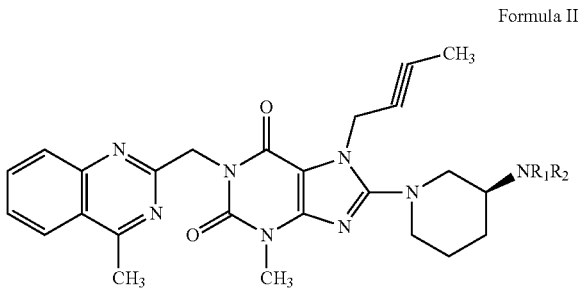

the process comprising reacting a compound of Formula III, wherein X is a halogen, with a compound of Formula IV;

Formula III

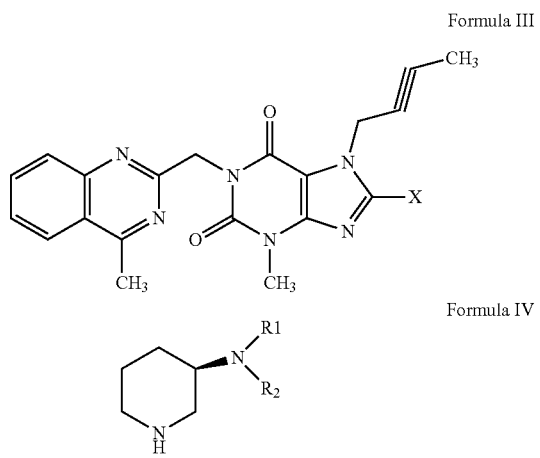

Formula IV wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

The reaction of compound of Formula III with compound of Formula IV may be carried out in the presence of a base. The base may be selected from an organic base and an inorganic base. The inorganic base may be selected from the group consisting of alkali metal hydroxides such as sodium hydroxide, potassium hydroxide, barium hydroxide and lithium hydroxide and the like; metal carbonates such as sodium carbonate, potassium carbonate, magnesium carbonate, and calcium carbonate and the like; metal bicarbonates such as sodium bicarbonate, and potassium bicarbonate; metal hydrides such as lithium hydride, sodium hydride, and potassium hydride and the like; borohydrides such as sodium borohydride, potassium borohydride; and bases such as lithium aluminium hydride and ammonia. The organic base may be selected from the group consisting of organic amines such as triethylamine, diisopropylethylamine, N,N-dimethylaniline, pyridine, 4-dimethylaminopyridine, tri-n-butylamine, N-methylmorpholine, piperidine and the like; alkali metal alkoxides such as sodium methoxide, sodium ethoxide, sodium-tert-butoxide, potassium methoxide, potassium ethoxide, potassium-tert-butoxide lithium methoxide, lithium ethoxide, lithium-tert-butoxide and the like.

The reaction of compound of Formula III with compound of Formula IV may be carried out in the presence of a solvent selected from the group consisting of alcohols, glycols, ethers, ketones, dimethylformamide, dimethylsulfoxide, sulfolane, N-methylpyrrolidone and the like.

The alcohol may be selected from the group consisting of methanol, ethanol, propanol, isopropanol, butanol, 2-butanol, isobutanol, pentanol and the like or mixtures thereof. The glycols may be selected from ethylene glycol, propylene glycol and the like. The ethers may be selected from the group consisting of dioxane, diethyl ether, tetrahydrofuran, tetrahydropyran, ethylenene glycol monomethylether, ethylene glycol diethylether and the like.

The reaction of compound of Formula III with compound of Formula IV may be carried out at room temperature or reflux temperature of the solvent used.

In one embodiment, the present invention provides a process for the preparation of a compound of Formula IIA, wherein the aromatic ring of the phthalimido group is substituted with one or more $R_3$ substituents selected from the group consisting of halogen, alkyl, nitro, amino, the Formula IIA

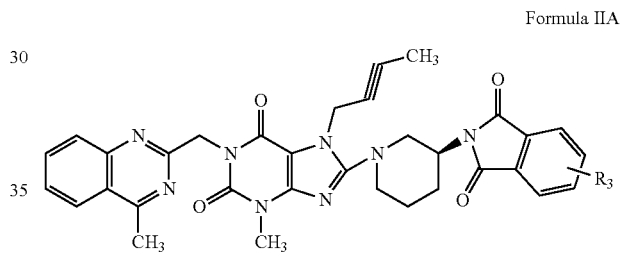

process comprising reacting a compound of Formula III, wherein X is a halogen, with a compound of Formula IVA, wherein the aromatic ring of the phthalimido group is substituted with one or more substituents selected from the group consisting of halogen, alkyl, nitro and amino.

Formula III

Formula IVA

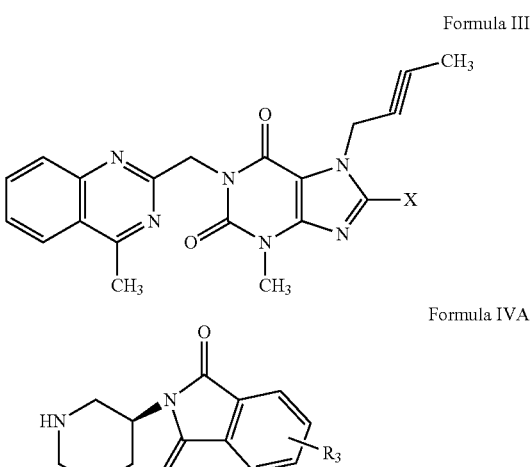

In one embodiment, the present invention provides a process for the preparation of a compound of Formula IIA, wherein $R_3$ is alkyl, the process comprising reacting a compound of Formula III, wherein X is halogen with a compound of Formula IVA, wherein $R_3$ is alkyl.

In one preferred embodiment, the present invention provides a process for the preparation of a compound of Formula IIA1, the

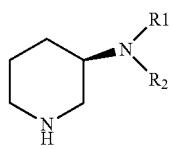

Formula IIA1 process comprising reacting a compound of Formula III, wherein X is halogen with a compound of Formula IVA1

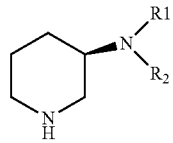

Formula IVA1

Preferably, X is bromine in the compound of Formula III and the reaction is carried out in the presence of dimethyl formamide and an inorganic base such as potassium carbonate.

In one preferred embodiment, the present invention provides a process for the preparation of a compound of Formula IIA1, the process comprising reacting a compound of Formula III, wherein X is halogen with a compound of Formula IVA1 in N-methylpyrrolidone and diisopropylethylamine.

The compound of formula IIA1 may be purified in a solvent selected from alcohols or halogenated hydrocarbons or mixtures thereof.

In one embodiment the compound of formula IIA1 may be purified from methanol.

In one embodiment the compound of formula IIA1 may be purified from methanol and methylene dichloride.

The present invention provides a compound of Formula IV;

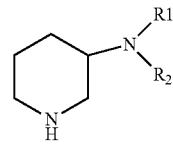

Formula IV wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl.

The present invention provides a compound of Formula IVA;

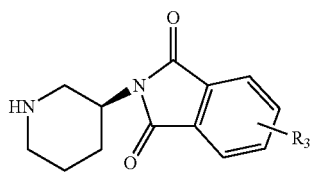

Formula IVA wherein the aromatic ring of the phthalimido group is substituted with one or more $R_3$ substituents selected from the group consisting of halogen, alkyl, nitro and amino.

The present invention provides a compound of Formula IVA, wherein $R_3$ is alkyl.

Specifically the present invention provides a compound of Formula IVA1

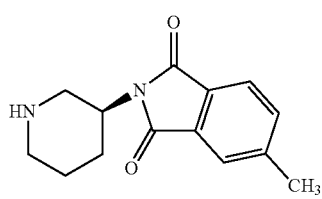

Formula IVA1

The present invention provides a process for the preparation of a compound of Formula IV;

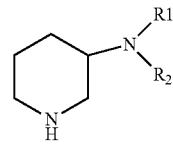

Formula IV wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino; or $R_1$ is H and $R_2$ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl; the process comprising resolving a racemic compound of Formula V, wherein $R_1$ and $R_2$ are same as above, with an optically active acid.

Formula V

The present invention provides a process for the preparation of a compound of Formula IVA;

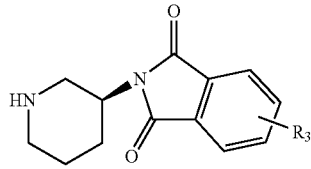

Formula IVA wherein the aromatic ring of the phthalimido group is substituted with one or more R₃ substituents selected from the group consisting of halogen, alkyl, nitro and amino; the process comprising resolving a racemic compound of Formula VA,

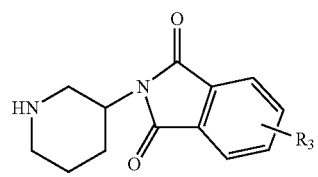

Formula VA with an optically active acid.

The present invention provides a process for the preparation of compound of Formula IVA wherein R₃ is alkyl; the process comprising resolving a racemic compound of Formula VA, wherein R₃ is alkyl, with an optically active acid.

In one embodiment, the present invention provides a process for the preparation of a compound of Formula IVA1,

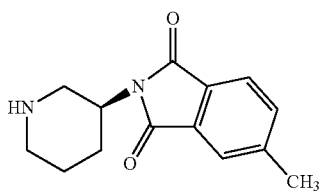

Formula IVA1 the process comprising resolving a racemic compound of Formula VA1, with an optically active acid

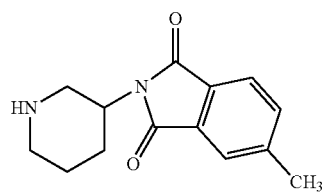

Formula VA1

The optically active acid for resolution may be selected from the group consisting of S-(+) mandelic acid, R-(−) mandelic acid, L-(+)tartaric acid, D-(−)tartaric acid, L-malic acid, D-malic acid, D-maleic acid, (−)-naproxen, (+)-naproxen, (+)-ibuprofen; (−)ibuprofen, (1R)-(−)-camphor sulfonic acid, (1S)-(+)-camphor sulfonic acid, (1R)-(+)-bromocamphor-10-sulfonic acid, (1S)-(−)-bromocamphor-10-sulfonic acid, (−)-Dibenzoyl-L-tartaric acid, (−)-Dibenzoyl-L-tartaric acid monohydrate, (+)-Dibenzoyl-D-tartaric acid monohydrate, (+)-dipara-tolyl-D-tartaric acid, (−)-dipara-tolyl-L-tartaric acid, L(−)-pyroglutamic acid, L(+)-pyroglutamic acid, (−)-lactic acid, L-lysine and D-lysine and the like. Preferably the optically active acid is selected from L-(+)tartaric acid, D-(−)tartaric acid, (−)-Dibenzoyl-L-tartaric acid, (−)-Dibenzoyl-L-tartaric acid, (+)-dipara-tolyl-D-tartaric acid, (−)-dipara-tolyl-L-tartaric acid.

In one embodiment, the present invention provides a process for the preparation of a compound of Formula IVA1,

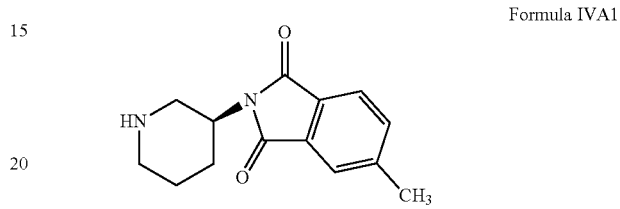

Formula IVA1 the process comprising
(a) treating a racemic compound of Formula VA1, with an optically active acid to form a mixture of diasteromeric salts;
(b) separating the desired diasteromeric salt, a compound of Formula VI, from the mixture of diasteromeric salts; and

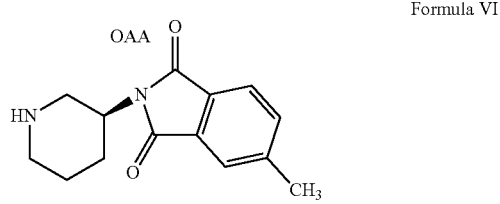 [SMILES: Cc1ccc2c(c1)C(=O)N([C@H]1CCCNC1)C2=O ; "OAA"]

Formula VI (c) treating the compound of Formula VI with a base to obtain a compound of Formula IVA1.

The term "OAA" in the compound of Formula VI is used to denote an optically active acid.

The optically active acid may be selected from the acids discussed supra. Preferably the optically active acid is selected, from L-(+)tartaric acid, D-(−)tartaric acid, (−)-Dibenzoyl-L-tartaric acid, (−)-Dibenzoyl-L-tartaric acid, (+)-dipara-tolyl-D-tartaric acid, (−)-dipara-tolyl-L-tartaric acid.

The diastereomeric mixture of salts obtained by the reaction of a racemic compound of Formula VA1 with the optically active acid may be separated based on differential solubility in solvents and the compound of Formula IVA1 may be obtained by treating the separated diasteromeric salt of compound of Formula VI with a base.

The bases used may be selected from the group consisting of ammonia, hydroxides such as sodium hydroxide, potassium hydroxide, carbonates such as sodium carbonate, potassium carbonate, lithium carbonate, alkoxides such as potassium methoxide, sodium methoxide, tert-butoxide, and bicarbonates such as sodium bicarbonate, potassium bicarbonate.

The undesired enantiomer may be optionally racemized and again converted to the desired enantiomer.

In one embodiment, the present invention provides a process for the preparation of a compound of Formula IV, wherein R₁ is H and R₂ is selected from the group consisting of trialkylsilyl, 2-trialkylsilylethoxycarbamates, acetyl, trihaloacetyl, 9-fluorenylmethoxycarbonyl, trityl, alkylsulfonyl, arylsulfonyl, diphenylphosphine and sulfonylethoxycarbonyl,

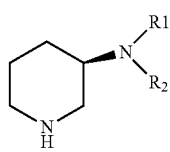

Formula IV the process comprising reacting R-(3)-aminopiperidine with trialkylsilylamine, 2-trialkylsilylethoxy carbamate, trihaloacetamide, 9-fluorenylmethoxycarbonyl derivative, trityl derivative, alkylsulfonamide, arylsulfonamide, diphenylphosphine derivative and sulfonylethoxycarbonyl derivative respectively.

In one embodiment, the present invention provides a process for the preparation of compound of Formula IVA

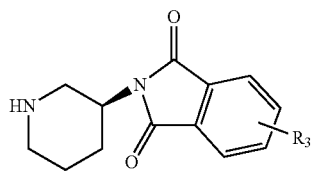

Formula IVA wherein the aromatic ring of the phthalimido group is substituted with one or more R₃ substituents selected from the group consisting of halogen, alkyl, nitro and amino; the process comprising reacting R-(3)-aminopiperidine with substituted phthalic anhydride wherein the aromatic ring of the phthalic anhydride is substituted with one or more R₃ substituents selected from the group consisting of halogen, alkyl, nitro and amino.

In one embodiment, the present invention provides a process for the preparation of compound of Formula IVA1, the process comprising reacting R-(3)-aminopiperidine with 4-methylphthalic anhydride.

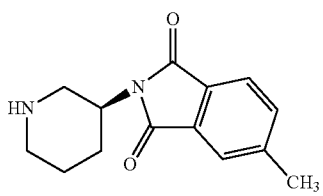

Formula IVA1

In another aspect, the present invention provides a process for the preparation of compound of Formula IIA1

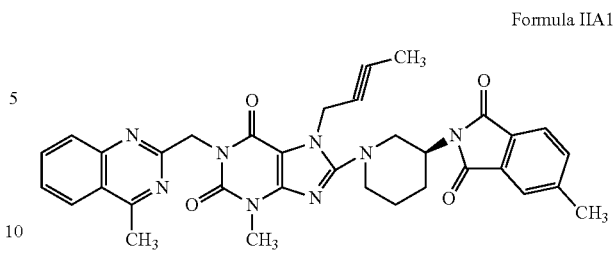

Formula IIA1 the process comprising reacting a compound of Formula III, wherein X is halogen with a compound of Formula VI

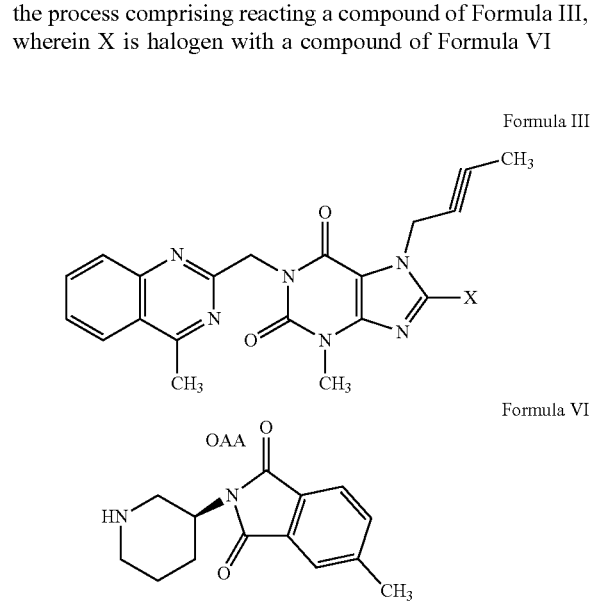

Formula III

Formula VI

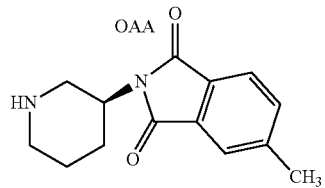

The reaction of a compound of Formula III with a compound of Formula VI may be carried out in the presence of a base. The base may be selected from an organic base and an inorganic base. The reaction of compound of Formula III with compound of Formula VI may be carried out in the presence of a solvent selected from the group consisting of alcohols, glycols, ethers, ketones, dimethylformamide, dimethylsulfoxide, sulfolane, N-methylpyrrolidone and the like.

The present invention provides the preparation of the starting compound of Formula V, the process comprising reacting 3-aminopiperidine with substituted phthalic anhydride, trimethylsilylamine, 2-trimethylsilylethoxy carbamate, trihaloacetamide, 9-fluorenylmethoxycarbonyl derivative, trityl derivative, alkylsulfonamide, arylsulfonamide, diphenylphosphine derivative and sulfonylethoxycarbonyl derivative. The present invention provides the preparation of the compound of Formula VA1, the process comprising reacting 3-aminopiperidine with alkyl substituted phthalic anhydride specifically the compound of Formula VA2 may be prepared by reacting 3-aminopiperidine with 4-methyl phthalic anhydride.

In one embodiment, the present invention provides linagliptin dibenzoyl-D-tartaric acid salt.

In one embodiment, the present invention provides crystalline linagliptin dibenzoyl-D-tartaric acid salt.

In one embodiment, the present invention provides crystalline linagliptin dibenzoyl-D-tartaric acid salt characterized by XRD pattern as depicted in FIG. 1.

In one embodiment, the present invention provides crystalline linagliptin dibenzoyl-D-tartaric acid salt characterized by XRD pattern having peak reflections at about 6.35, 7.52, 14.05±0.2 degrees 2 theta.

In one embodiment, the present invention provides linagliptin ditoluoyl-D-tartaric acid salt.

In one embodiment, the present invention provides use of Linagliptin dibenzoyl-D-tartaric acid for the preparation of linagliptin.

In one embodiment, the present invention provides use of Linagliptin dibenzoyl-D-tartaric acid for the preparation of linagliptin with a chiral purity of at least 99.95% as determined by HPLC.

In one embodiment, the present invention provides a process for preparing pure linagliptin comprising
 a. converting the linagliptin into linagliptin dibenzoyl-D-tartaric acid salt;
 b. treating the linagliptin dibenzoyl-D-tartaric acid salt with a suitable base to form linagliptin; and
 c. isolating the pure linagliptin.

The reaction of linagliptin with dibenzoyl-D-tartaric acid to form linagliptin dibenzoyl-D-tartaric acid salt may be carried out in alcoholic solvents such as methanol. If required the linagliptin dibenzoyl-D-tartaric acid salt may be purified using isopropanol.

In one embodiment the linagliptin dibenzoyl-D-tartaric acid salt is converted to linagliptin by treatment with an organic or inorganic base such as sodium hydroxide, potassium hydroxide and the like.

In one embodiment the present invention provides linagliptin having chemical purity greater than 99.6% as determined by High performance liquid chromatography (HPLC). In one embodiment the present invention provides linagliptin having compound of formula IIA1 less than 0.15% as determined by HPLC. In one embodiment the present invention provides linagliptin having compound of formula III less than 0.15% as determined by HPLC. In one embodiment the present invention provides linagliptin having compound of formula IVA1 less than 0.15% as determined by HPLC.

In one embodiment die present invention, provides linagliptin having impurity X observed in HPLC at relative retention time of 2.29 and having mass m/z value of 716 as characterized by mass spectrometry in less than 0.15% as determined by HPLC. Preferably less than 0.05%. In one embodiment the present invention provides linagliptin substantially free of impurity X.

HPLC methodology: Reagents, Solvents and Standards: Water (Milli Q or equivalent) Acetonitrile (HPLC grade), Sodium perchlorate (GR Grade) Perchloric acid (70%) (GR Grade) Chromatographic Conditions: Apparatus: A High Performance Liquid Chromatograph equipped with quaternary gradient pumps, variable wavelength UV (detector attached with data recorder and integrator software. Column: Inertsil ODS 3V, 250×4.6 mm, Column temperature: 30° C. Sample Cooler temperature: 25° C. Mobile Phase: Mobile Phase A=Buffer: Acetonitrile (80:20, v/v) Buffer: 0.01 M Sodium perchlorate in water. Adjust pH 4.0 with 5% Perchloric acid in water. Mobile Phase B=Buffer:Acetonitrile (20:80, v/v) Diluent: Buffer:Acetonitrile (1:1, v/v) Flow Rate: 1.0 mL/minute Detection: UV 225 nm Injection Volume: 20 µL. The retention time of linagliptin is about 9.2 minutes under these conditions. Relative retention time for impurity X with respect to the main peak is 2.29.

In one embodiment the present invention provides linagliptin having chiral purity greater than 99.98% as determined by HPLC.

In one embodiment the present invention provides linagliptin having a chemical purity of at least 99.6% and chiral purity of 99.95% as determined by HPLC.

In one embodiment the present invention provides linagliptin having chemical purity greater than 99.6% and chiral purity greater than 99.98% as determined by HPLC.

In one aspect, the present invention provides a process for the preparation of alogliptin, the process comprising reacting a compound of Formula VII wherein X is halogen, with a compound of Formula IVA1 to obtain compound of formula VIII, followed by deprotecting the compound of Formula VIII.

Formula VII

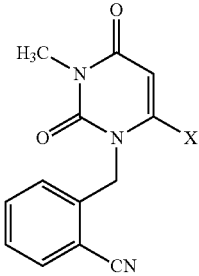

Formula IVA1

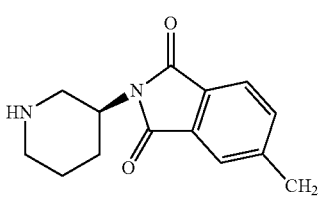

Formula VIII

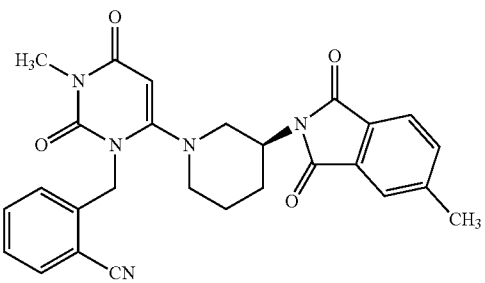

In another embodiment, the present invention provides a polymorphic mixture, comprising at least about 0.5 weight %, based on the total weight of the mixture, of polymorph Form A or polymorph Form B of linagliptin, with the remaining amount of the mixture being the other polymorph form of linagliptin. In another embodiment, the present invention provides a polymorphic mixture, comprising at least about 1 weight %, based on the total weight of the mixture, of polymorph Form A or polymorph Form B of linagliptin, with the remaining amount of the mixture being the other polymorph form of linagliptin. In another embodiment, the present invention provides a polymorphic mixture, comprising at least about 2.5 weight %, based on the total weight of the mixture, of polymorph Form A or polymorph Form B of linagliptin, with the remaining amount of the mixture being the other polymorph form of linagliptin. In another embodiment, the present invention provides a polymorphic mixture, comprising at least about 5 weight %, based on the total weight of the mixture, of polymorph Form A or polymorph Form B of linagliptin, with the remaining amount of the mixture being the other polymorph form of linagliptin. In yet another embodiment, the present invention provides a polymorphic mixture, comprising at least about 10 weight %, based on the total weight of the mixture, of polymorph Form A or polymorph Form B of linagliptin, with the remaining amount of the mixture being the other polymorph form of linagliptin. In yet another embodiment, the present invention provides a polymorphic mixture, comprising at least about 15 weight, based on the total weight of the mixture, of polymorph Form A or polymorph Form B of linagliptin, with the remaining amount of the mixture being the other polymorph form of linagliptin. In yet another embodiment, the present invention provides a polymorphic mixture, comprising at least about 20 weight %, based on the total weight of the mixture, of polymorph Form A or polymorph Form B of linagliptin, with the remaining amount of the mixture being the other polymorph form of linagliptin. In yet another embodiment, the present invention provides a polymorphic mixture, comprising at least about 25 weight %, based on the total weight of the mixture, of polymorph Form A or polymorph Form B of linagliptin, with the remaining amount of the mixture being the other polymorph form of linagliptin.

In yet another embodiment, the present invention provides a polymorphic mixture, comprising about 25 weight % to about 90 weight % of polymorph Form A of linagliptin and about 75 weight % to about 10 weight % of polymorph Form B of linagliptin. In yet another embodiment, the present invention provides a polymorphic mixture, comprising about 80 weight % (±5%) of polymorph Form A of linagliptin and about 20 weight % (±5%) of polymorph Form B of linagliptin. In yet another embodiment, the present invention provides a polymorphic mixture, comprising about 70 weight % (±5%) of polymorph Form A of linagliptin and about 30 weight % (±5%) of polymorph Form B of linagliptin. In yet another embodiment, the present invention provides a polymorphic mixture, comprising about 60 weight % (±5%) of polymorph Form A of linagliptin and about 40 weight % (±5%) of polymorph Form B of linagliptin. In yet another embodiment, the present invention provides a polymorphic mixture, comprising about 50 weight % (±5%) of polymorph Form A of linagliptin and about 50 weight % (±5%) of polymorph Form B of linagliptin. In yet another embodiment, the present invention provides a polymorphic mixture, comprising about 40 weight % (±5%) of polymorph Form A of linagliptin and about 60 weight % (±5%) of polymorph Form B of linagliptin. In yet another embodiment, the present invention provides a polymorphic mixture, comprising about 30 weight % (±5%) of polymorph Form A of linagliptin and about 70 weight % (±5%) of polymorph Form B of linagliptin. In yet another embodiment, the present invention provides a polymorphic mixture, comprising about 75% of polymorph Form A of linagliptin and about 25% of polymorph Form B of linagliptin.

In yet another embodiment, the present invention provides a process for the preparation of a polymorphic mixture of Form A and Form B of linagliptin, the process comprising recrystallizing linagliptin in a solvent selected from the group consisting of $C_1$-$C_5$ alcohol, a $C_2$-$C_9$ ester, a $C_3$-$C_9$ ketone, a $C_3$-$C_5$ carbonate, nitriles, hydrocarbon solvents and halogenated derivatives thereof, ethers, acetic acid, dimethylformamide (DMF), dimethylacetamide (DMAC), N-methylpyrrolidine, formamide, N-methylacetamide, N-methylformamide, dimethylsulfoxide(DMSO), ethylformate, sulfonate, N,N-dimethylpropionamide, nitromethane, nitrobenzene, and hexamethylphosphoramide, and mixtures thereof and mixtures of said organic solvents and water.

The $C_1$-$C_5$ alcohol may be selected from the group consisting of methanol, ethanol, n-propanol, isopropanol, n-butanol, isobutanol, 2-butanol and the like. The $C_2$-$C_9$ ester may be selected from the group consisting of methyl acetate, ethyl acetate, isopropyl acetate, isobutyl acetate, n-butyl acetate, t-butyl acetate and the like. The $C_3$-$C_9$ ketone may be selected from the group consisting of acetone, 2-butanone, methylethyl ketone, ethylmethylketone, isopropylmethylketone, methyl isobutyl ketone and the like. The $C_3$-$C_5$ carbonate may be selected from the group consisting of dimethyl carbonate, diethyl carbonate and the like; nitriles such as acetonitrile, propionitrile and the like.

The hydrocarbon solvents and halogenated derivatives may be selected from the group consisting of pentane, hexane, heptane, cyclohexane, petroleum ether, toluene, benzene, cycloheptane, methylcyclohexane, ethylbenzene, m-, o-, or p-xylene, octane, indane, nonane, dichloromethane (MDC), chloroform, carbon tetrachloride, 1,2-dichloroethane and the like. The ethers may be selected from the group consisting of diethyl ether, dimethyl ether, dimethoxymethane, dimethoxypropane, isopropyl ether, di-isopropyl ether, methyl t-butyl ether, tetrahydrofuran (THF), dioxane, furan, ethylene glycol dimethyl ether, ethylene glycol diethyl ether, diethylene glycol dimethyl ether, diethylene glycol diethyl ether, anisole and the like.

In yet another embodiment, the present invention provides a process for the preparation of a mixture polymorphic Form A and B of linagliptin, the process comprising recrystallizing linagliptin in a solvent selected from the group consisting of $C_1$-$C_5$ alcohol, ethers, esters, dimethylsulfoxide and mixtures thereof or their mixture with water.

In yet another embodiment, the present invention provides a process for the preparation of a mixture polymorphic Form A and B of linagliptin, the process comprising recrystallizing linagliptin in ethyl acetate.

In yet another embodiment, the present invention provides a process for the preparation of a mixture polymorphic Form A and B of linagliptin, the process comprising recrystallizing linagliptin in isopropyl alcohol.

In yet another embodiment, the present invention provides a process for the preparation of a mixture polymorphic Form A and B of linagliptin, the process comprising recrystallizing linagliptin in dimethylsulfoxide and water mixture.

In yet another embodiment, the present invention provides a process for the preparation of linagliptin, the process comprising recrystallizing linagliptin from a mixture of methylene dichloride and methyl t-butyl ether.

In yet another embodiment, the present invention provides a process for the preparation of a mixture polymorphic Form A and B of linagliptin, the process comprising recrystallizing linagliptin from a mixture of methylene dichloride and methyl t-butyl ether.

In yet another embodiment, the present invention provides a process for the preparation of a mixture of polymorphic Form A and B of linagliptin, the process comprising recrystallizing linagliptin from a mixture of methanol and methyl t-butyl ether.

In one embodiment the present invention provides a process for the preparation of a mixture of polymorphic Form A and B of linagliptin, the process comprising heating linagliptin in methanol at reflux temperature adding methyl t-butyl ether at reflux temperature and stirring the reaction mass at refluxing temperature for a period of about 30 mins to 1 hour and cooling the reaction mixture slowly at room temperature.

In one embodiment the present invention provides a process for the preparation of a mixture of polymorphic Form A and B of linagliptin, the process comprising heating linagliptin in methanol at reflux temperature adding methyl t-butyl ether at reflux temperature and stirring the reaction mass at refluxing temperature for a period of about 30 mins to 1 hour and cooling the reaction mixture slowly at room temperature and seeding the reaction mixture with a mixture of polymorphic form A and B to isolate a mixture of polymorphic Form A and B of linagliptin.

In one embodiment the present invention provides a process for the preparation of a mixture of polymorphic Form A and B of linagliptin, the process comprising heating linagliptin in methanol at reflux temperature adding methyl t-butyl ether at reflux temperature and stirring the reaction mass at refluxing temperature for a period of about 30 mins to 1 hour and cooling the reaction mixture slowly at room temperature and seeding the reaction mixture with polymorphic B to isolate a mixture of polymorphic Form A and B of linagliptin.

In yet another embodiment, the present invention provides a process for the preparation of polymorphic Form C of linagliptin, the process comprising recrystallizing linagliptin from a mixture of methanol and methyl t-butyl ether.

In one embodiment the present invention provides a process for the preparation of polymorphic Form C of linagliptin, the process comprising heating linagliptin in methanol at reflux temperature, cooling the reaction mass to a temperature in the range of about 0° C. to about 15° C. and adding methyl t-butyl ether and stirring the reaction mass.

The following examples are provided to enable one skilled in the art to practice the invention and are merely illustrative of the invention. The examples should not be read as limiting the scope of the invention as defined in the features and advantages.

EXAMPLES

Example 1

Preparation of (R)—N-piperidin-3-ylacetamide Dibenzoyl Tartarate Salt (a) Preparation of N-(pyridin-3-yl)-acetamide In a RBF 500 ml of tetrahydrofuran (THF), 100 gm of 3-amino pyridine were charged under nitrogen atmosphere. Added 130 gm of acetic anhydride at about 0-5° and maintained the reaction mass for about 17 hr at room temperature to complete the reaction. Distilled off the THF below about 45° C. under vacuum. Charged 2000 ml of diisopropylethylamine and heated the reaction mass to about 50° C. for about 30 min. Cooled the reaction mass to room temperature and filtered the product and then washed with 200 ml DIPEA. Dried the product at about 45-50°.

(b) Preparation of N-piperidin-3-yl-acetamide

In an autoclave 500 ml of acetic acid, 100 gm of N-(pyridin-3-yl)-acetamide and 20 gm of 10% Pd/C were charged. 10 kg hydrogen pressure was applied to the reaction mass and the temperature was raised to about 80° C. Maintained the reaction mass for about 5.0 hrs and after completion of the reaction, the reaction mass was filtered through Hyflobed. Acetic acid was distilled off under vacuum below about 55° C. to get an oily mass. The oily mass was dissolved in 1000 ml of methylene dichloride and the pH adjusted to about 10-12 by using sodium hydroxide solution. The salt was filtered and washed with 300 ml methylene dichloride. Distilled off the methylene dichloride under vacuum below 35° C. to get an oil. Wt of Oil 95.0 gm (c) Preparation of (R)—N-piperidin-3-ylacetamide Dibenzoyl tartarate salt In a RBF charged 500 ml of Methanol, 50 gm of N-piperidin-3-ylacetamide & 138 gm of L (+)-Dibenzoyl tartaric acid. The reaction was maintained for about 90 mins at room temperature and then heated to reflux. The reaction mass was maintained for about an hour at reflux and then cooled and maintained at room temperature for about 12.0 hours. Then, the product was filtered and washed with 100 ml methanol. Again charged the obtained wet cake in 800 ml methanol, heated to reflux and maintained reaction mass for 1.0 hr to get a clear solution. Cooled the reaction mass to room temperature and maintained for 12.0 hrs. The product was filtered and washed with 100 ml methanol. The product was dried at about 45-50° C. under vacuum. Unwanted S-isomer NMT 1.5% Dry Wt-20. Gm.

Example 2

Preparation of R-3-(4-Methylphthalimido)-piperidine (a) Preparation of 3-Aminopiperdine dihydrochloride In a clean round bottom flask, 400 ml of Conc HCl and 100 gm of N-piperidin-3-ylacetamide (prepared in Ex 1 b) were charged & refluxed for 4 hours. The reaction mass was concentrated to get thick oil. 500 ml ethanol was added to the oil & stirred at room temperature to get solid. Dry wt 100 gms (b) Preparation of 3-(4-Methylphthalimido)piperidine In a clean round bottom flask, 30 ml acetic acid, 10 gms 3-aminopiperidine dihydrochloride & 14 gms 4-methylphthalic anhydride were charged. The reaction mass was refluxed for 1 hour & then cooled to 60° C. The reaction mass was concentrated to get the oily mass. 100 ml ethanol was added to reaction mass. The reaction mass was heated to 78-80° C. to get uniform slurry. The reaction mass was cooled to room temp & filtered to get the titled compound. Dry wt 8.5 gms.

(c) Resolution of 4-Methylphthalimido-3-piperidine

Method 1:
In a clean round bottom flask, 1.0 gms 3-(4-Methylphthalimido)piperidine & 5 ml acetic acid were charged. A solution of D(−)-tartaric acid in 5 ml ethanol was added to the reaction mass at about 85-90° C. & stirred for 30 minutes. The reaction mass was cooled to RT & filtered & washed with 2 ml ethanol to obtain a solid. The solid was taken in water and the pH was adjusted to 8-10 using liquid ammonia. Methylene dichloride was added to the aqueous layer. The organic layer was separated and the product isolated from the organic layer.

Method 2:
In a clean round bottom flask, 1.0 gms 3-(4-Methylphthalimido)piperidine & 10 ml ethyl acetate were charged. A solution of dibenzoyl tartaric acid in 5 ml ethyl acetate was added to the reaction mass at 78-82° C. & stirred for 30 minutes. The reaction mass was cooled to RT & filtered & washed with 2 ml ethyl acetate. 10 ml ethyl acetate was added to the obtained wet cake & heated at reflux for about 1.0 hr to get uniform slurry. The reaction mass was cooled to RT & maintained for 12.0 hrs. The product was filtered & washed with 2 ml ethyl acetate. The solid was taken in water and the pH was adjusted to 8-10 using sodium hydroxide. Methylene dichloride was added to the aqueous layer. The organic layer was separated and the product isolated from the organic layer Example 3

Preparation of 3-(R)-4-Methylphthalimido)piperidine (a) Preparation of 3-(R)-Aminopiperidine dihydrochloride In a clean round bottom flask, 400 ml of Conc HCl and 100 gm of N-piperidin-3-(R)-ylacetamide dibenzoyl tartarate salt (prepared in Ex 1 c) were charged & refluxed for 4 hours. The reaction mass was concentrated to get thick oil. Added 500 ml ethanol to the oil & stirred at RT to get solid. Dry wt 100 gms (b) 3-(R)-(4-Methylphthalimido)piperidine In a clean round bottom flask, 30 ml acetic acid, 10 gms 3-(R)-aminopiperidine dihydrochloride & 14 gms 4-methylphthalic anhydride were charged. The reaction mass was refluxed for 1 hour & then cooled to 60° C. The reaction mass was concentrated to get the oily mass. 100 ml ethanol was added to reaction mass. The reaction mass was heated to 78-80° C. to get uniform slurry. The reaction mass was cooled to room temperature & filtered to get the titled compound.

Example 4

Preparation of 1-[(4-Methylquinazolin-2-yl)methyl]-3-methyl-7-(2-butin-1-yl)-8-(3-(R)-4-methylphthalimidopiperidin-1-yl-xanthine In a clean round bottom flask 5 gms of 1-[4-methylquinazolin-2yl)-methyl]-3-methyl-7-(2-but-1-nyl)-8-bromoxanthine, 4.0 gms of (R-)3-(4-methylphthalimido)-piperidine, 0.9 gms of potassium carbonate & 50 ml of dimethylformamide were charged. The reaction mass was maintained at about 80° C. for about 12 hrs. The reaction mass was cooled to about room temperature and 100 ml water was added. Then, the product was extracted with 50 ml methylene dichloride. The methylene dichloride layer was concentrated and the product was isolated in methyl tertiary butyl ether. Dry wt 4 gms.

Example 5

Preparation of 1-[(4-Methylquinazolin-2-yl)methyl]-3-methyl-7-(2-butin-1-yl)-8-(3-(R)-4-methylphthalimidopiperidin-1-yl)-xanthine In a clean round bottom flask, 1 gm of 1-[4-methylquinazolin-2yl)-methyl]-3-methyl-7-(2-but-1-nyl)-8-bromoxanthine, 1.3 gms of 3-(R)-(4-methylphthalimido)-piperidine tartrate salt, 0.5 gms of potassium carbonate & 10 ml of dimethylformamide were charged. The reaction mass was maintained at about 80° C. for 12 hrs. The reaction mass was cooled to about room temperature & 20 ml water was added & the product extracted with 20 ml methylene dichloride. The methylene dichloride layer was concentrated & the product was isolated in methyl tertiary butyl ether. Dry wt 1.09 gms.

Example 6

Preparation of Linagliptin

In a RBF 1 ml of toluene, 100 mg of 1-[(4-Methylquinazolin-2-yl)methyl]-3-methyl-7-(2-butin-1-yl)-8-(3-(R)-4-methylphthalimidopiperidin-1-yl)-xanthine, 0.1 ml of ethanolamine were charged, the temperature was raised to about 100-110° C. and the reaction mass was maintained for about 3 hours to complete the reaction. After the completion of the reaction, the reaction mass was cooled to about 80° C. The aqueous and oil layers were separated. The aqueous layer was extracted again with 1 ml of toluene. The organic layers were combined and washed with 2 ml of water at about 80° C. The organic layer was concentrated under vacuum to get an oily mass. Added 2 ml water to the oily mass and adjusted the pH to about 2-3 using aq. HCl. The aqueous layer was washed with methylene dichloride (MDC). The pH of aqueous layer was adjusted to about 10-12 using 5% aq NaOH solution. The product was extracted in MDC and worked up by either of the methods (a), (b) or (c) listed below (a) MDC layer was concentrated & product was isolated by methanol. Dry wt 50 mg. HPLC purity>99.0%. (b) MDC layer was concentrated & product was dissolved in a mixture of 5 ml acetone & 5 ml ethyl acetate at 40-45° C. Reaction mass cooled to RT & filtered. Wet cake was washed with 2 ml mixture of ethyl acetate & acetone. Dry wt 40 mg. HPLC purity>99.0%. (c) MDC layer was concentrated & product was dissolved in 10 ml IPA at 40-45° C. Reaction mass cooled to RT & filtered. Wet cake was washed with 2 ml IPA. Dry wt 60 mg. HPLC purity>99.0%.

Example 7

Preparation of Linagliptin

In a clean round bottom flask, 9 ml of ethanol, 90 mg of 1-[(4-Methylquinazolin-2-yl)methyl]-3-methyl-7-(2-butin-1-yl)-xanthine & 0.9 ml of hydrazine hydrate were charged. The temperature of the reaction mass was raised to 78-80° C. & the reaction mass was maintained for 3 hours. The reaction mass was cooled to 50° C. & ethanol was distilled off. 9 ml methylene dichloride was added to the obtained residue & stirred at RT to get the solid. Undesired solid was filtered. The filtrate was concentrated & 9 ml methyl tert butyl ether was added to the residue to get the solid Linagliptin. Reaction mass was stirred at RT & filtered. Wet cake was washed with 2 ml IPA. Dry wt 45 mg Example 8

Crystallization of Linagliptin 0.50 gm of Linagliptin and 2.5 ml of ethanol was charged into a clean and dried round bottom flask and refluxed for about 30 min. Subsequently the solution was slowly cooled to about 20° C. No precipitate was observed at about 20° C. Further, the solution was cooled to below 10° C. and the precipitation was observed. 5.0 ml of MTBE added and stirred for 60 min below 10° C. The mixture is filtered and dried under vacuum at ambient temperature.

Example 9

Crystallization of Linagliptin 2.00 gm of Linagliptin and 10.0 ml of ethanol was charged in to a clean and dried round bottom flask and refluxed for about 1.5 min. Subsequently the solution is slowly cooled to about 25° C. Further, the solution was cooled to below 0° C. and maintained for about an hour and precipitation was observed. Thereafter, 20.0 ml of MTBE added and stirred for about 60 min below about 10° C. The mixture was filtered and dried under reduced pressure below 10° C.

Example 10

Crystallization of Linagliptin 0.10 gm of Linagliptin and 0.30 ml of dimethylsulfoxide (DMSO) was charged in to a clean and dried round bottom flask and warmed for about 5 min to get a clear solution. The mixture was quenched in 25 volume of water and stirred overnight. Reaction mixture was filtered and dried under reduced pressure ambient temperature.

Example 11

Crystallization of Linagliptin 0.10 gm of Linagliptin and 10.0 ml of isopropanol was charged into a clean and dried round bottom flask and refluxed for about 15 min. Subsequently the solution was slowly cooled to about 25° C. Further, the solution was stirred and maintained for about 2 hr and precipitation was observed. The mixture was filtered and dried under reduced pressure at about 25-30° C. overnight.

Example 12

Crystallization of Linagliptin 1 g of linagliptin was recrystallized from a mixture of 5 ml of ethyl acetate and 5 ml of acetone.

Example 13

Preparation of 3-(R)-4-Methylphthalimido)piperidine

In a clean round bottom flask, 100 ml acetic acid, 50 gms 3-(R)-aminopiperidine dihydrochloride & 56.5 gms of 4-methylphthalic anhydride were charged. The reaction mass was refluxed & then cooled to 25-30° C. Acetone was added to the reaction mass & obtained solid was filtered. Acetone was added to the solid obtained & refluxed to get uniform slurry. The reaction mass was cooled to 25-30° C. & filtered. Wet wt 70 gms. In another round-bottom flask, methylene dichloride, wet cake and water were charged. The reaction mass was basified & layers were separated. The organic layer was washed with water & concentrated upto half volume. Diisopropyl ether was added to the reaction mass to obtain the product Dry wt 40 gms, HPLC purity=85%

Example 14

Preparation of 3-(R)-4-Methylphthalimido)piperidine

In a clean round bottom flask, 1000 ml methanol and 200 gm 3-(R)-aminopiperidine dihydrochloride were charged. Cooled the reaction mass to 0-10° C. and added 1850 ml 2.5% methanolic NaOH solution slowly at 0-10° C. Stirred and filtered the inorganic solid, distilled out clear filtrate under vacuum below 45° C. Added 400 ml acetic acid and cooled the reaction mass to room temperature, added 226.1 gm 4-methylphthalic anhydride. Reaction mass was refluxed & then cooled to 25-30° C. Acetone was added to the reaction mass & obtained solid was filtered. Acetone was again added to the solid obtained & refluxed to get uniform slurry. The reaction mass was cooled to 25-30° C. & filtered. Dry wt: 280 gms. In another round bottom flask, above dried solid material, methylene dichloride and water were charged. The reaction mass was basified & layers were separated. The organic layer was washed with water & concentrated upto half volume. Diisopropyl ether was added to the reaction mass to obtain the product
Dry wt: 175 gms,
HPLC purity=96.16%

Example 15

Preparation of 1-[4-Methylquinazolin-2yl-methyl]-3-methyl-7-(2-but-1-nyl)-8-bromoxanthine In a round bottom flask, 140 ml DMF, 20 gm of 8-bromo-7-but-2-yn-1-yl-methyl-3,7-dihydro-1H-purine-2,6-dione and 15.67 gm of 2-(chloromethyl)-4-methyl-1,2-dihydroquinazoline were charged. 14 gm potassium carbonate was added to the reaction mass and heated to 95-100° C. for 3 hours. The reaction mass was cooled to 0-10° C. & added 100 ml water. The reaction mass was allowed to come to 25-30° C. The solid obtained was filtered & the slurry was washed with water. The obtained solid was purified in ethyl acetate to get the product. Dry wt 25 gms, HPLC purity=98%

Example 16

Preparation of 1-[(4-Methylquinazolin-2-yl)methyl]-3-methyl-7-(2-butin-1-yl)-8-(3-(R)-4-methylphthalimidopiperidin-1-yl)-xanthine In a clean round bottom flask 40 ml N-Methyl-2-Pyrrolidone (NMP), 10 gm 8-bromo-7-(but-2-yn-1-yl)-3-methyl-1-[(4-methylquinazolin-2-yl)methyl]-3,7-dihydro-1H-purine-2,6-dione and 8.1 gm 4-methyl-3-(R)-pthalimidopiperidine were charged. The temperature of the reaction mass was raised to 80-85° C. & 10 ml diisopropylamine was added. The reaction mass was heated to 100-105° C. & maintained at this temp to complete the reaction. On completion of reaction, reaction mass was cooled to 35-40° C. & methanol was added. The reaction mass was further cooled to 25-30° C. & filtered. Obtained wet material was again purified in methanol to get the product. Dry wt 10 gms, HPLC purity=97%

Example 17

Preparation of 1-[(4-Methylquinazolin-2-yl)methyl]-3-methyl-7-(2-butin-1-yl)-8-(3-(R)-4-methylphthalimidopiperidin-1-yl)xanthine In a clean round bottom flask 680 ml N-Methyl-2-Pyrrolidone (NMP), 170 gm 8-bromo-7-(but-2-yn-1-yl)-3- methyl-1-[(4-methylquinazolin-2-yl)methyl]-3,7-dihydro-1H-purine-2,6-dione and 138 gm 4-methyl-3-(R)-pthalimidopiperidine were charged. The temperature of the reaction mass was raised to 80-85° C. & 170 ml diisopropylamine was added. The reaction mass was heated to 100-105° C. & maintained at this temp. On completion of reaction, the reaction mass was cooled to 35-40° C. & methanol was added. The reaction mass was further cooled to 25-30° C. & filtered. The wet material obtained was again slurried in methanol to get the crude product, wet wt: 287 gm. In another round bottom flask, 595 ml methanol, 255 ml MDC and crude wet cake were charged. The reaction mass was heated to reflux and then cooled to room temperature. The solid obtained was filtered and washed with methanol to get the pure product. Dry wt: 162 gms, HPLC purity=98.77%

Example 18

Preparation of Linagliptin Crude

In a clean round bottom flask, 10 gm of 1-[(4-Methylquinazolin-2-yl)methyl]-3-methyl-7-(2-butin-1-yl)-8-(3(R)-4-methylphthalimidopiperidine-yl)-xanthine and 100 ml of toluene were charged. 10 ml of ethanolamine was added to the reaction mass and heated to 90-95° C. to complete the reaction. The reaction mass was cooled to 80° C. and the layers were separated. The organic phase was distilled under vacuum to get crude linagliptin. Dry wt: 7.50 gm HPLC purity: 97.95% Impurity X: 0.69%

Example 19

Preparation of Linagliptin Crude

In a clean round bottom flask, 10 gm of 1-[(4-Methylquinazolin-2yl)methyl]-3-methyl-7-(2-butin-1yl)-8-(3(R)-4-methyl phthalimidopiperidine-yl)-xanthine and 100 ml of toluene were charged, 10 ml of ethanolamine was added to the reaction mass and heated to 75-80° C. to complete the reaction. The reaction mass was cooled to 50-55° C. Water was added to reaction mass & layers were separated. Organic phase was distilled under vacuum to get Linagliptin crude. Dry wt: 7.50 gm Example 20

Preparation of Linagliptin

In a clean round bottom flask, 10.0 gms of 1-[(4-Methylquinazolin-2yl) methyl]-3-methyl-7-(2-butin-1yl)-8-(3(R)-4-methyl phthalimidopiperidine-yl)-xanthine and 50 ml ethanolamine were charged. The reaction mass was heated to 90-100° C. for 1 hr and cooled to room temperature. 100 ml water was added and the solid was filtered. 150 ml of toluene was added and completely distilled out under vacuum at 45-50° C. to get pale yellow solid. Dry wt: 6.0 gm.
Yield: 78.94%, (molar yield) Purity: 98.83%.

Example 21

Preparation of Linagliptin Dibenzoyl-D-tartaric Acid Salt

In a clean round bottom flask, 7.5 gm of crude linagliptin and 100 ml methanol were charged. A solution of 5.81 gm Di-benzoyl-D-Tartaric acid in 100 ml methanol was added at 60° C. and the reaction mass was stirred for 1.0 hr. The reaction mass was cooled to room temperature and the obtained salt was filtered and washed with 20 ml methanol. Dry wt: 12.0 gm HPLC purity: 99.54%, Impurity X: 0.20%

Example 22

Purification of Linagliptin Dibenzoyl-D-tartaric Acid Salt

In a clean round bottom flask, 12 gm of Linagliptin dibenzoyl-D-tartaric acid salt and 120 ml isopropanol were charged. The reaction mass was heated to reflux & maintained for 1.0 hr at reflux. The reaction mass was cooled to room temperature and stirred for 1.0 hr. The solid was filtered and washed with isopropanol. Dry Wt: 11.70 gm, HPLC purity: 99.63%, Impurity X: 0.08%.
$^1$H NMR (400 MHz) of Linagliptin dibenzoyl-D-tartaric acid salt: 1.03-1.04 (d, 2H), 1.57 (m, 2H), 1.76-1.77 (incompletely resolved, s, 3H,) superimposed with 1.77 (m, 1H), 1.93 (m, 1H), 2.88 (s, 3H), 3.0-3.12 (m, 2H), 3.32-3.33 (m, 1H), 3.46-3.49, (dd, 1H), 3.65-3.67 (dd, 1H), 4.83-4.95 (m, 2H), 5.33 (s, 2H), 5.66 (s, 2H), 7.47-8-28 (4+10H).
XRD Table of Linagliptin Dibenzoyl-D-tartaric Acid Salt

| Pos [°2θ] | d spacing [Å] | Rel. Int % | Pos [°2θ] | d spacing | Rel. Int % |
|---|---|---|---|---|---|
| 2.08 | 42.37 | 2.24 | 12.75 | 6.94 | 30.78 |
| 6.35 | 13.91 | 100.00 | 13.29 | 6.66 | 14.43 |
| 7.62 | 11.59 | 83.66 | 14.05 | 6.30 | 67.57 |
| 9.34 | 9.47 | 16.61 | 14.46 | 6.13 | 21.19 |
| 10.94 | 8.09 | 27.27 | 15.05 | 5.89 | 26.20 |
| 11.35 | 7.80 | 9.39 | 15.84 | 5.60 | 7.53 |
| 11.77 | 7.52 | 14.80 | 16.56 | 5.35 | 8.08 |
| 12.14 | 7.29 | 10.99 | | | |

Differential Scanning Calorimetric (DSC) thermogram having an endotherm peak at about 233±0.2° C. The TGA shows a weight loss of 0.6% upto 150° C. over a range of 0-250° C.

Example 23

Preparation of Linagliptin

In a clean round bottom flask, 150 gms Linagliptin dibenzoyl-D-tartaric acid salt, 1500 ml water and 1500 ml MDC were charged. The reaction mass was basified with 5% aq. NaOH solution and the layers were separated. The organic layer was washed with water and distilled out under vacuum below 40° C. to get pale yellow semisolid. 150 ml methanol was added and heated to 60-65° C. to get a clear solution. The reaction mass was cooled to 50-55° C. and 1200 ml methyl tert-butyl ether was added slowly at this temperature. The slurry obtained was stirred for 30 min at 50-55° C. and then cooled to room temperature, filtered and washed with 150 ml methyl tert-butyl ether to obtain a mixture of Form A and Form B of Linagliptin. Dry wt: 80 gm Related substance by HPLC: Compound of formula III: not detected, Compound of formula IIA1: not detected; HPLC Purity: 99.85%; S-isomer by HPLC: 0.02%

Example 24

Preparation of Linagliptin

In a clean round bottom flask, 10 gm of Linagliptin dibenzoyl-D-tartaric acid salt and 100 ml methylene dichloride were charged. 100 ml water was added and pH was adjusted to 8-10 by adding 5% Aq. NaOH. The reaction mass was stirred at room temperature for 30 min. and the layers were separated. The organic layer was distilled under vacuum and pure linagliptin was isolated from a 120 ml mixture of methylene dichloride and methyl tert butyl ether. Dry Wt: 5.50 gm HPLC purity: 99.64%, Impurity X: 0.06% Chiral Purity: Unwanted isomer: 8-[3(S)-Aminopiperidin-1-yl]-7-(2-butynyl)-3-methyl-1-(4-methylquinazolin-2-ylmethyl)xanthine, NMT 0.02%

Example 25

Preparation of Form-C of Linagliptin

In a clean round bottom flask, 2.0 gms Linagliptin and 20 ml methanol were charged. The reaction mass was heated to 50-55° C. to get a clear solution. Reaction mass was cooled to 5-10° C. and added 20 ml methyl tert-butyl ether slowly at 5-10° C. Stirred for 30 min at 5-10° C. and filtered, washed with 4 ml methyl tert-butyl ether. Dry wt: 1.6 gm Example 26

Preparation of Form-C of Linagliptin

In a clean round bottom flask, 2.0 gms Linagliptin and 20 ml methanol were charged. The reaction mass was heated to 50-55° C. to get clear solution. Reaction mass was cooled to 5-10° C. and added 40 ml methyl tert-butyl ether slowly at 5-10° C. Stirred for 30 min at 5-10° C. and filtered, washed with 4 ml methyl tert-butyl ether. Dry wt: 1.6 gm Example 27

Preparation of Form-A of Linagliptin

In a clean round bottom flask, 10 gms Linagliptin dibenzoyl-D-tartaric acid salt, 100 ml water and 100 ml MDC were charged. The reaction mass was basified with 5% aq. NaOH solution and layers were separated. Organic layer was washed with water and distilled out under vacuum at 40° C. to get pale yellow semisolid. 20 ml ethanol was added and heated to reflux to get a clear solution. Reaction mass was cooled to 55-60° C. and added 40 ml methyl tert-butyl ether. Stirred for 30 min at 55-60° C. and cooled to room temperature, filtered and washed with 20 ml methyl tert-butyl ether. Dry wt: 5.30 gm HPLC purity: 99.66%

Example 28

Preparation of Linagliptin in Toluene and Ethanolamine Using 1-[(4-Methylquinazolin-2yl) methyl]-3-methyl-7-(2-butin-1yl)-8-(3(R)-4-methyl phthamidopiperidine-yl)-xanthine In a clean round bottom flask, 10.0 gms of 1-[(4-Methylquinazolin-2yl) methyl]-3-methyl-7-(2-butin-1yl)-8-(3 (R)-4-methyl phthalimidopiperidine-yl)-xanthine and 100 ml toluene were charged. 11 ml of ethanolamine was added and the reaction mass was heated to 100-105° C. for 3 hrs. The reaction mass was cooled to 80-85° C. and the layers were separated. The organic layer was washed with 100 ml water and distilled out the organic layer completely under vacuum at 45-50° to get pale yellow solid. Yield: 90%, Purity: 97.49%.

Comparative Example

Preparation of Linagliptin in Toluene and Ethanolamine Using 1-[(4-methylquinazolin-2yl) methyl]-3-methyl-7-(2-butin-1yl)-8-(3(R)-phthalmidopiperidine-yl)-xanthine Intermediate In a clean round bottom flask, 5.0 gms of 1-[(4-Methylquinazolin-2yl) methyl]-3-methyl-7-(2-butin-1yl)-8-(3 (R)-phthalimidopiperidine-yl)-xanthine and 50 ml toluene were charged. 10 ml ethanolamine was added and the reaction mass was heated to 100-105° C. for 2 hrs. The reaction mass was cooled to 80° C. and the layers were separated. The organic layer was distilled out completely under vacuum at 45-50° C. and the product isolated in 25 ml methyl tert butyl ether to get pale yellow solid. Dry wt: 1.80 gm. Yield: 46.15%, Purity: 94.98%.

It was observed that the linagliptin obtained by using unsubstituted phthalimidopiperidine as exemplified in the comparative example has a lower purity and the yield of linagliptin obtained is very low as compared to the linagliptin obtained by the process of the present invention using substituted phthalimidopiperidine compound of formula IIA1 (example 28).

The invention claimed is:

1. Crystalline linagliptin dibenzoyl-D-tartaric acid salt.
2. The linagliptin dibenzoyl-D-tartaric acid salt of claim 1 in crystalline form characterized by an XRD pattern having peak reflections at 6.35, 7.52, 14.05±0.2 degrees 2 theta.
3. The linagliptin dibenzoyl-D-tartaric acid salt of claim 1 in crystalline form characterized by a $^1$H NMR spectrum having peaks at δ 1.03-1.04 (d, 2H), 1.57 (m, 2H), 1.76-1.77 (s, 3H,), 1.93 (m, 1H), 2.88 (s, 3H), 3.0-3.12 (m, 2H), 3.32-3.33 (m, 1H), 3.46-3.49 (dd, 1H), 3.65-3.67 (dd, 1H), 4.83-4.95 (m, 2H), 5.33 (s, 2H), 5.66 (s, 2H), and 7.47-8.28 (4+10H).
4. The crystalline linagliptin dibenzoyl-D-tartaric acid salt of claim 1, characterized by Differential Seaming calorimetric (DSC) thermogram having an endotherm peak at 233±0.2° C.
5. A process for the preparation of crystalline linagliptin dibenzoyl-D-tartaric acid salt comprising reacting linagliptin with dibenzoyl-D-tartaric acid.

* * * * *